United States Patent [19]

Martin et al.

[11] Patent Number: 4,897,403

[45] Date of Patent: Jan. 30, 1990

[54] ANTIMALARIAL COMPOSITIONS AND METHODS

[75] Inventors: Samuel K. Martin, Silver Spring; Ayo M. J. Oduola, Gaithersburg; Wilbur K. Milhous, Rockville, all of Md.

[73] Assignee: The United States of America as represented by the Secretary of the Army, Washington, D.C.

[21] Appl. No.: 936,677

[22] Filed: Nov. 18, 1986

[51] Int. Cl.[4] .................. A61K 31/47; A61K 31/275; A61K 31/44

[52] U.S. Cl. .................................... 514/313; 514/523; 514/895; 514/356

[58] Field of Search ........................ 514/313, 523, 895

[56] References Cited

U.S. PATENT DOCUMENTS 3,082,154 3/1963 Allan .................................... 167/82
3,574,833 4/1971 Arnold et al. ....................... 424/229
3,663,693 5/1972 Slighter et al. ..................... 424/229
4,284,627 8/1981 Raether et al. ..................... 514/313

FOREIGN PATENT DOCUMENTS 2177913A 2/1987 United Kingdom ................ 514/313

OTHER PUBLICATIONS

Chemical Abstracts, 77:168620r (1972).

*Primary Examiner*—Jerome D. Goldberg
*Attorney, Agent, or Firm*—Werten F. W. Bellamy

[57] ABSTRACT

An antimalarial composition contains as the active ingredient a mixture of a chemical compound effective in reversing the resistance of cancer cells to chemotherapy drugs and at least one antimalarial agent. A method for treating malaria in mammals comprises administering a composition containing the active ingredient. A method for reducing the resistance of a malarial parasite to an antimalarial agent comprises administering a composition containing the active ingredient.

2 Claims, 2 Drawing Sheets

ANTIMALARIAL COMPOSITIONS AND METHODS

FIELD OF THE INVENTION

The present invention relates to improved compositions and methods for treating malaria. The invention specifically relates to compositions and methods for treating malaria caused by malarial parasites, which are resistant to conventional antimalarial agents.

BACKGROUND OF THE INVENTION

Many conventional antimalarial agents are known for treating malaria in mammals. For example, U.S. Pat. Nos. 3,082,154 to Allan, 3,574,833 to Arnold et al, 3,663,693 to Slighter et al and 4,284,627 to Raether et al disclose known antimalarial agents and compositions. Known antimalarial agents include mefloquine (a 4-quinolinemethanol), chloroquine and quinine. However, the widespread eradication of malaria with conventional antimalarial agents such as chloroquine and the other recited agents does not appear possible owing to the emergence of malarial parasites which are resistant to conventional antimalarial agents. For example, chloroquine resistant *Plasmodium falciparum,* which first appeared in Columbia and Thailand in 1960, is rapidly spreading. In fact, by 1984, chloroquine resistant *P. falciparum* had rapidly spread to at least 15 countries in Eastern Asia and Oceania, 10 countries in South America and 15 countries in Africa south of the Sahara. While mefloquine first appeared to be effective for treating resistant malarial parasites such as the chloroquine resistant *P. falciparum,* treatment failures with mefloquine have been reported. Isolates of *P. falciparum* from Thailand have been shown in vitro to be resistant to mefloquine, chloroquine and quinine. In face, isolates of *P. falciparum* have demonstrated resistance to antimalarial drugs to which the parasite is not known to have been previously exposed. Similar patterns of cross resistance and multiple drug resistance have been observed during laboratory induction of drug resistance in cloned strains of *P. falciparum.* Accordingly, a need exists to provide compositions and methods for effectively treating malarial parasites, and particularly for treating malarial parasites which exhibit resistance to one or more conventional antimalarial agents.

Multiple drug resistance patterns have also been encountered in cancer chemotherapy treatments. Neoplastic cells have become resistant not only to the drug used in the chemotherapy treatment but also to other unrelated drugs. The basis for this resistance in neoplastic cells has been actively studied in the last decade, and recent studies suggest that enhanced active efflux prevents the drug to which the cell is resistant from reaching toxic levels within the cell cytosol. Additionally, it has recently been determined that various chemical compounds have the effect of inhibiting enhanced active efflux so that the drug can accumulate in the cell whereby drug resistance is reversed and the resistant cell becomes sensitive again. Among the chemical compounds which have the effect of inhibiting the active efflux of chemotherapy drugs from cancer cells are calcium channel blockers.

SUMMARY OF THE INVENTION

It has now been discovered that the chemical compounds which have been determined to be effective in reversing the drug resistance of cancer cells to chemotherapy drugs are also effective in reversing the resistance of malarial parasites to antimalarial drugs.

It is therefore an object of the present invention to provide an antimalarial composition for combating malarial parasites. It is an additional object of the invention to provide an antimalarial composition for combating malarial parasites which are resistant to treatment with conventional antimalarial agents. It is an additional object of the invention to provide an antimalarial composition for treating malaria in mammals and, particularly, to provide an antimalarial composition for treating malaria in mammals caused by malarial parasites which are resistant to conventional antimalarial agents. Further objects according to the present invention comprise providing methods for treating malaria in mammals and methods for reducing the resistance of malarial parasites to conventional antimalarial agents.

The aforementioned objects and advantages are provided according to the present invention by an antimalarial composition containing as the active ingredient a mixture of a chemical compound which has been determined as being effective in reducing drug resistance in cancer cells and at least one conventional antimalarial agent. The composition preferably comprises a chemical compound such as a calcium channel blocker which has been determined to be effective in reversing drug resistance in cancer cells and at least one antimalarial agent. The antimalarial agent comprises a conventional antimalarial agent and, preferably, may comprise chloroquine, mefloquine, quinine, their therapeutically acceptable salts or mixtures thereof. The combination of a chemical compound shown to be effective in reducing or reversing drug resistance in cancer cells with the antimalarial agent reverses and reduces the resistance of malarial parasites to the antimalarial agent.

Further objects of the invention are provided by the method according to the present invention for treating malaria in mammals. The method comprises administering to the mammal infected with malaria an antimalarially effective amount of a composition containing as the active ingredient a mixture of a chemical compound shown to be effective in reducing or reversing drug resistance in cancer cells and at least one antimalarial agent. The present invention also relates to a method for reducing the resistance of a malarial parasite to an antimalarial agent by administering to a mammal infected with the malarial parasite the composition according to the present invention containing as the active ingredient a mixture of a chemical compound shown to be effective in reducing or reversing drug resistance in cancer cells and the antimalarial agent.

These and additional objects and advantages of the present invention will become more apparent from the following detailed description.

BRIEF DESCRIPTION OF THE DRAWING

The following detailed description will be more fully understood in view of the accompanying drawings in which.

DETAILED DESCRIPTION

Figure 1:
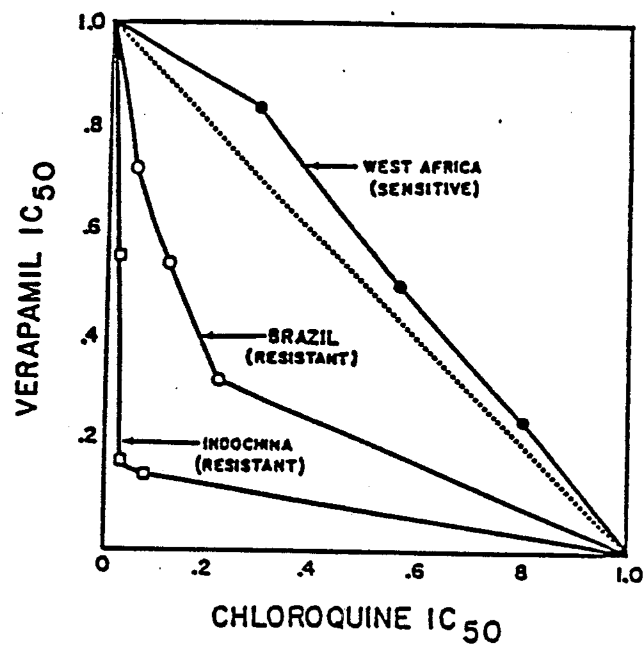
FIG. 1 comprises an isobologram setting forth concentration response data generated from verapamil and chloroquine used in constant ratios of their $IC_{50}$'s as set forth in Example 1.

The antimalarial compositions according to the present invention contain as the active ingredient a mixture of a chemical compound known to be effective in reducing or reversing drug resistance in cancer cells and at least one antimalarial agent. Hereinafter, the chemical compounds known to be effective in reducing or reversing drug resistance in cancer cells will be referred to as the "reversing compounds". The combination of the reversing compound and the antimalarial agent reverses and reduces the resistance of a malarial parasite to the antimalarial agent. Thus, the compositions according to the present invention are particularly effective for treating malaria in mammals caused by malarial parasites which are resistant to conventional antimalarial agents.

The reversing compounds useful in the compositions and methods of the present invention are those which have been determined to be effective in reducing or reversing the resistance of cancer cells to chemotherapy drugs. A preferred group of reversing compounds comprises calcium channel blockers.

Verapamil is one calcium channel blocker particularly adapted for use in the composition of the present invention. Nifedipine is another calcium channel blocker preferred for use in the composition of the present invention. Other known calcium channel blockers may also be included as well as mixtures thereof.

Antimalarial agents which are useful in combination with the reversing compound according to the present invention include conventional antimalarial agents known in the art. Conventional antimalarial agents which are known in the art include chloroquine, quinine, mefloquine, primaquine, pyrimethamine, cycloguanil, trimethoprim, sulfadoxine, dapsone, their therapeutically acceptable salts, or mixtures thereof. Preferred antimalarial agents for use in the compositions according to the present invention include chloroquine, mefloquine, quinine, their therapeutically acceptable salts and mixtures thereof. A particularly preferred antimalarial agent comprises chloroquine. Suitable therapeutically acceptable salts are also well known in the art, such as chloroquine diphosphate and chloroquine disulfate.

The ratios of reversing compound and the antimalarial agent which are included in the composition according to the present invention may be easily determined by one of ordinary skill in the art depending on the particular malarial parasite which is to be treated and the particular body which is infected therewith. Generally, the antimalarial composition will include the reversing compound and the antimalarial agent in a molar ratio of from about 10:1 to about 10,000:1.

The antimalarial composition may be administered orally or parenterally. For oral administration, tablets, capsules, powders or granules which contain as the active ingredient the mixture of the reversing compound and at least one antimalarial agent may be used together with the usual excipients and adjuvants such as starch, cellulose powder, talcum magnesium stearate, sugar, gelatine, calcium carbonate, finely divided sicilic acid, carboxymethyl cellulose or similar substances. For parenteral administration, various sterile suspensions may be used, such as oily suspensions prepared from fatty oils such as olive oil, sesame oil, peanut oil, castor oil or a synthetic triglyceride, or aqueous suspensions prepared from ethoxylated sorbitane fatty acid esters, polyethylene glycol or carboxymethyl cellulose. These preparations and suspensions for administering the antimalarial compositions according to the present invention are well known in the art.

The method for treating malaria in mammals according to the present invention comprises administering to a mammal infected with malaria an antimalarially effective amount of the compositions according to the present invention which contain as the active ingredient a mixture of the reversing compound and at least one antimalarial agent. The antimalarial composition reduces the resistance of the malarial parasite to the antimalarial agent and allows the antimalarial agent to combat the parasite.

The following examples demonstrate the effectiveness of the compositions and methods according to the present invention. Throughout the examples, incorporation of radiolabelled hypoxanthine was used to measure a synchronous growth of the malarial parasites and inhibition of incorporation was the measured parameter of the parasites' rsponse to the drugs. Semi-automated microdilution techniques as disclosed by R. E. Desjardins et al, *Antimicrob. Agents Chemother,* 16, 710 (1979) were used to determine the in vitro susceptibilities of a chloroquine-sensitive West African clone (D-6) and two chloroquine-resistant clones, one from Indochina (W-2) and one from Brazil (IEC 306).

EXAMPLE 1

First, the antimalarial properties of verapamil (a calcium channel blocker "reversing compound") in vitro were studied. Although 1,000 fold less potent than chloroquine or mefloquine, verapamil demonstrated an inhibitory concentration ($IC_{50}$) of 6–8 micrograms/ml which is similar to that of tetracycline. The action of a mixture of verapamil and chloroquine against the chloroquine sensitive West African clone and the chloroquine resistant clones from Indochina and Brazil was then asssessed. Fifty percent inhibitory concentrations were calculated from concentration response data which was generated for each verapamil and chloroquine alone and in combination generally in accordance with the semi-automated microdilution technique of Desjardins et al, supra. The drug combinations were dosed in fixed ratios of their 50% inhibitory concentrations. Two fold dilutions were made of a starting concentration containing 50 nM chloroquine (CQ) and 50 uM verapamil (VER), 25 nm CQ+75 uM VER; and 75 nM CQ+25 uM VER. The results are set forth in Table 1.

TABLE 1

| | FIFTY PERCENT INHIBITORY CONCENTRATION ($IC_{50}$) | | | | |
|---|---|---|---|---|---|
| | SINGLE DRUGS | | | | |
| | CHLOROQUINE | VERAPAMIL | DRUG COMBINATIONS | | |
| CLONE | nM | μM | CQ 50 nM/VER 50 μM | CQ 25 nM/VER 75 μM | CQ 75 nM/VER 25 μM |
| W. Africa D-6 | 14.1 | 15.7 | 8.0/8.0 | 4.4/13.2 | 11.4/3.8 |
| Indochina W-2 | 41.9 | 8.0 | 1.3/1.3 | 1.5/4.4 | 3.8/1.3 |
| Brazil IEC-306 | 52.3 | 11.5 | 6.3/6.3 | 2.8/8.3 | 11.7/3.9 |

The control $IC_{50}$ of each of verapamil and chloroquine was normalized to one unit of $IC_{50}$ and plotted on the ordinate and abscissa, respectively, of the isobologram set forth in FIG. 1. The $IC_{50}$'s of each drug in combination set forth in Table 1 were then calculated as a fraction of the control $IC_{50}$ and plotted as a fraction of one unit of $IC_{50}$ in FIG. 1. Thus, the isobologram of FIG. 1 graphically depicts whether the $IC_{50}$ of one drug (chloroquine) is reduced, unchanged or increased in the presence of the second drug (verapamil). The line connecting each unit of $IC_{50}$ for each clone represents the additivity of drug effects. Accordingly, the inward bowing of the curves representing the clones from Indochina and Brazil shows that the combination of the reversing compound verapamil and chloroquine produced a synergistic effect against the chloroquine resistant material parasite clones. That is, a mixture of the reversing compound verapamil and chloroquine provided significantly improved treatment effects against the malarial parasite clones as compared with either compound alone.

EXAMPLE 2

This example assesses the interaction of the reversing compound verapamil and chloroquine by generating concentration response data. The concentration response data was generated for the chloroquine sensitive West African clone and the chloroquine resistant clones from Indochina and Brazil using (1) chloroquine alone, and (2) chloroquine in the presence of constant sub-inhibitory concentrations of the reversing compound verapamil. Specifically, chloroquine was combined with sub-inhibitory concentrations of the reversing compound verapamil equal to $1\times10^{-6}$M and $2\times10^{-6}$M which alone showed no significant effects on malarial parasite growth or hypoxanthine uptake in vitro. The generated concentration response data is set forth in Table 2.

TABLE 2

| EFFECT OF VERAPAMIL ON CHLOROQUINE SENSITIVITY OF *P. FALCIPARUM* CLONES | | | | |
|---|---|---|---|---|
| | | ($IC_{50}$ + 1SD) | | |
| CLONE | | CHLOROQUINE ALONE | CHLOROQUINE + $1 \times 10^{-6}$ M VER | CHLOROQUINE + $2 \times 10^{-6}$ M VER |
| W. Africa CQ Sensitive | D-6 | 8.6 ± 0.3 | 7.8 ± 0.6 | 8.8 ± 0.3 |
| Indochina CQ Resistant | W-2 | 46.5 ± 2.5 | 8.4 ± 0.4 | 5.6 ± 0.3 |

Figure 2:
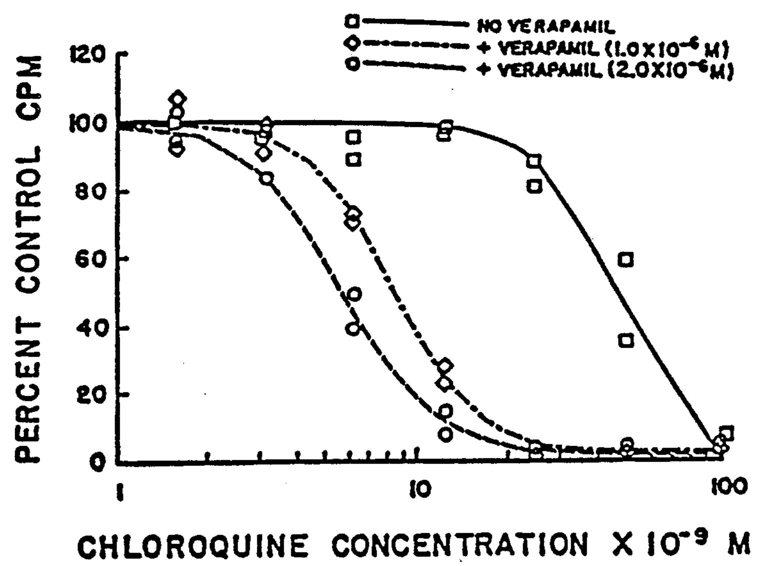
FIG. 2 is a graphical representation of concentration response data for a chloroquine resistant clone using chloroquine alone and chloroquine in the presence of constant sub-inhibitory concentrations of verapamil as set forth in Example 2.
Figure 3:
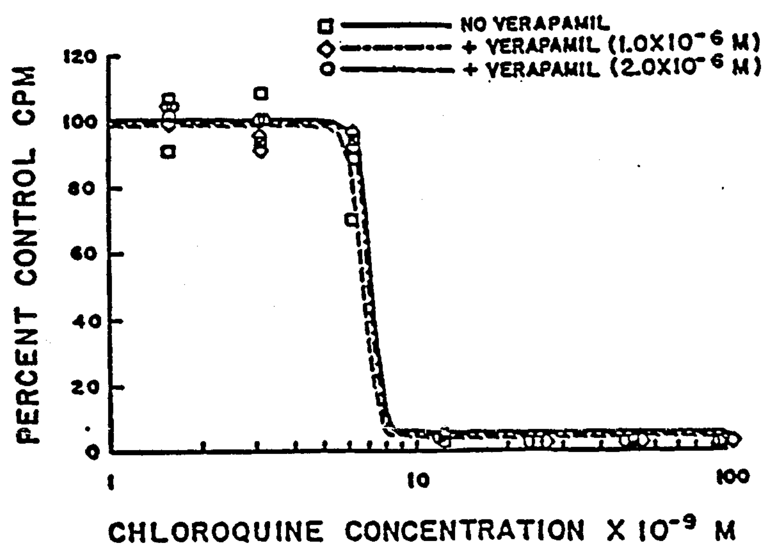
FIG. 3 is a graphical representation of concentration response data for a chloroquine sensitive clone using chloroquine alone and chloroquine in the presence of constant sub-inhibitory concentrations of verapamil as set forth in Example 2.

FIG. 2 graphically sets forth the response data derived with respect to the chloroquine resistant clone from Indochina while FIG. 3 graphically sets forth the response data derived with respect to the chloroquine-sensitive West African clone. As set forth in FIGS. 2 and 3, in the presence of a constant concentration of the reversing compound verapamil, the chloroquine-resistant clone was as sensitive to the chloroquine treatment as the chloroquine-sensitive West African clone.

Thus, the combination of a reversing compound as defined above with an antimalarial agent such as chloroquine reduces and reverses the resistance of a malarial parasite to the antimalarial agent. Thus, the antimalarial composition according to the present invention provides improvements for treating malaria caused by malarial parasites and particularly provides improvements for treating malaria caused by malarial parasites which are resistant to conventional antimalarial agents.

The preceding examples are set forth to illustrate specific embodiments of the invention and are not intended to limit the scope of the compositions and methods of the present invention. Additional embodiments and advantages within the scope of the claimed invention will be apparent to one of ordinary skill in the art.

What is claimed is:

1. An antimalarial composition containing as the active ingredient a mixture of verapamil and chloroguine or therapeutically acceptable salts of chloroquine, being present in a molar ratio of from about 10:1 to 20,000:1 respectively.

2. A method for treating malaria in mammals comprising administering to a mammal infected with malaria an antimalarially effective amount of a composition as defined in claim 1.

* * * * *